United States Patent [19]

Takabayashi et al.

[11] Patent Number: 5,817,087
[45] Date of Patent: Oct. 6, 1998

[54] SHORTS TYPE DISPOSABLE DIAPER

[75] Inventors: Keima Takabayashi; Shinobu Takei; Harumitsu Toyoda, all of Haga-gun, Japan

[73] Assignee: Kao Corporation, Tokyo, Japan

[21] Appl. No.: 911,023

[22] Filed: Aug. 13, 1997

Related U.S. Application Data

[63] Continuation of Ser. No. 656,362, filed as PCT/JP95/02022, Oct. 4, 1995 published as WO96/11656, Apr. 25, 1996.

[30] Foreign Application Priority Data

Oct. 14, 1994 [JP] Japan .................................. 6-249762
Jan. 31, 1995 [JP] Japan .................................. 7-014577

[51] Int. Cl.$^6$ ...................................................... A61F 13/15
[52] U.S. Cl. ........................................ 604/385.2; 604/393
[58] Field of Search ................................ 604/385.2, 393, 604/396

[56] References Cited

FOREIGN PATENT DOCUMENTS

| | | |
|---|---|---|
| 0570981 | 11/1993 | European Pat. Off. ................ 604/396 |
| 1141711 | 9/1989 | Japan . |
| 470288 | 4/1994 | Japan . |
| 2267024 | 11/1993 | United Kingdom ................... 604/396 |

*Primary Examiner*—Robert A. Clarke
*Attorney, Agent, or Firm*—Birch, Stewart, Kolasch & Birch, LLP

[57] ABSTRACT

A shorts type disposable diaper comprising an absorbent body which comprises a liquid permeable topsheet, a liquid impermeable backsheet, and an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, characterized in that the topsheet and/or the backsheet have a mechanical strength of about 1,500 gf/50 mm or more in the longitudinal direction of the diaper.

6 Claims, 4 Drawing Sheets

SHORTS TYPE DISPOSABLE DIAPER

This application is a continuation of application Ser. No. 08/656,362 filed on Jun. 14, 1996, now abandoned.

This application claims the benefit of priority of International Application PCT/JP95/02022, filed Oct. 4, 1995 published as WO96/11656, Apr. 25, 1996.

TECHNICAL FIELD

This invention relates to a shorts type disposable diaper having a front waist body portion and a rear waist body portion joined together.

BACKGROUND ART

Recently there is an increasing demand for shorts type disposable diapers chiefly for babies who begin to walk.

This seems to be because a conventional flat type diaper is hard to fit whereas a shorts type diaper can be put on simply by pulling it up while a baby is standing, affording great convenience to mothers.

However, a shorts type diaper is inconvenient when it is removed from a wearer after solid waste materials are discharged.

That is, a flat type diaper can easily be removed after use, even after solid waste materials are discharged, by detaching a fastening tape. In order to remove a shorts type diaper, on the other hand, the front waist body portion and the rear waist body portion should be torn apart at the joint (as a matter of course, a shorts type diaper may be taken off by pulling it down, but it is very likely that the waste materials will get on the wearer's leg). It is desirable that the front and rear portions be firmly joined while a diaper is worn because force tends to concentrate in the joint portion. A problem of conventional shorts type diapers is that the strength of the joint portion is so high that a considerable force is needed to manually tear the joint apart (the first problem).

As another problem, when the joint is to be torn apart, the materials of the diaper are torn off in the width direction, resulting in a substantial failure to tear apart. Further, other materials such as an elastic member (e.g., a rubber band) remains untorn. If one tries to manually tear off the elastic member by force, the elastic member extended to its full length strikes against one's hand, hindering the manual tearing action (the second problem).

In order to solve these problems, a diaper in which the joint portion has a specific seal pattern has been proposed in Japanese Utility Model Application Laid-Open 6-31721. According to this technique, a solution to the above-described first problem is provided, but the second problem still remains unsolved. Besides, the proposed seal pattern is complicated and makes the manufacturing process control laborious. It has also been proposed to specify the strength of the joint portion as an approach to the solution of the first problem, but neither does this proposal solve the second problem.

It has been proposed to perforate the side of the sealed part so as to improve tearability in a broad sense as disclosed in Japanese Utility Model Laid Open 1-141711. According to this proposal, although tearability is surely improved, there are some cases in which the diaper is torn at the perforations and removed from a wearer during use.

Under these circumstances, a technique which solves both of the above-described first and second problems has not yet been proposed, and such a technique has been desired.

DISCLOSURE OF THE INVENTION

It is therefore an object of the present invention to provide a shorts type disposable diaper which can easily be torn apart at the joint portion thereof and is therefore convenient for use.

The present invention provides a shorts type disposable diaper comprising an absorbent body which comprises a liquid permeable topsheet, a liquid impermeable backsheet, and an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, characterized in that the topsheet and/or the backsheet have a mechanical strength of 1,500 gf/50 mm or more in the longitudinal direction of the diaper (hereinafter referred to as a first invention), thereby achieving the above object of the present invention.

The present invention also provides a shorts type disposable diaper comprising an absorbent body which comprises a liquid permeable topsheet, a liquid impermeable backsheet, and an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, characterized in that said absorbent body has a covering sheet for covering elastic members, the covering sheet being disposed between the absorbent member and the backsheet; the opposing lateral side edges of each of said front and rear waist body portions are provided on the covering sheet and the backsheet; the opposing lateral side edges of each of said front and rear waist body portions are joined together in such a manner that opposing side edges of the covering sheet are brought into contact with each other; and either one of the covering sheet and the backsheet has a mechanical strength of 1,500 gf/50 mm or more in the longitudinal direction of the diaper (hereinafter referred to as a second invention), thereby achieving the above object of the present invention.

According to the present invention, at least one of the sheets constituting the joint portion formed by joining and sealing the opposing lateral side edges of the absorbent body has a high mechanical strength in the longitudinal direction of a diaper. Therefore, the diaper is not torn in the width direction when it is torn in a usual manner, and the joint portion of the diaper can easily be torn in the longitudinal direction.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Preferred embodiments of the present invention will be described in detail by referring to the accompanying drawings.

To begin with, an embodiment of the shorts type disposable diaper according to the first invention is illustrated with reference to FIGS. 1 through 5.

Figure 1:
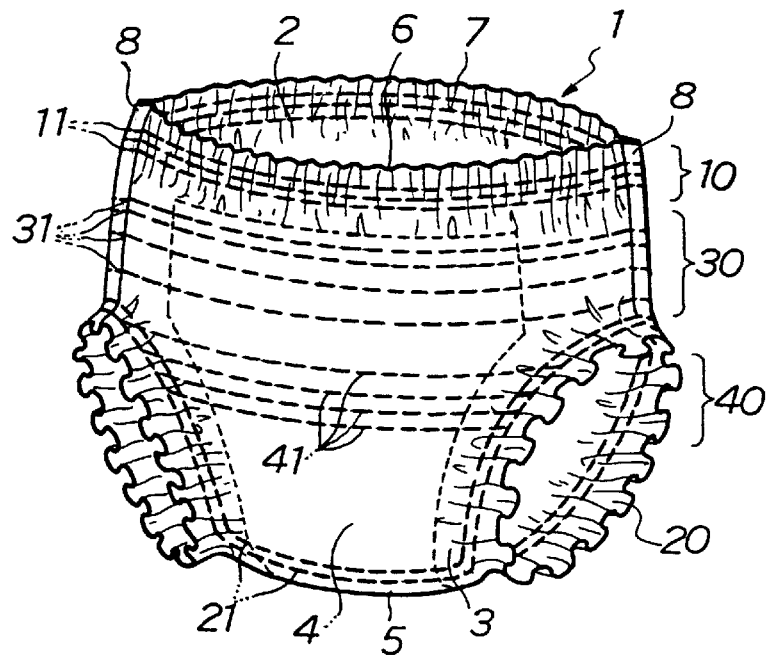
FIG. 1 is a perspective view of a shorts type disposable diaper according to the first invention.
Figure 2:
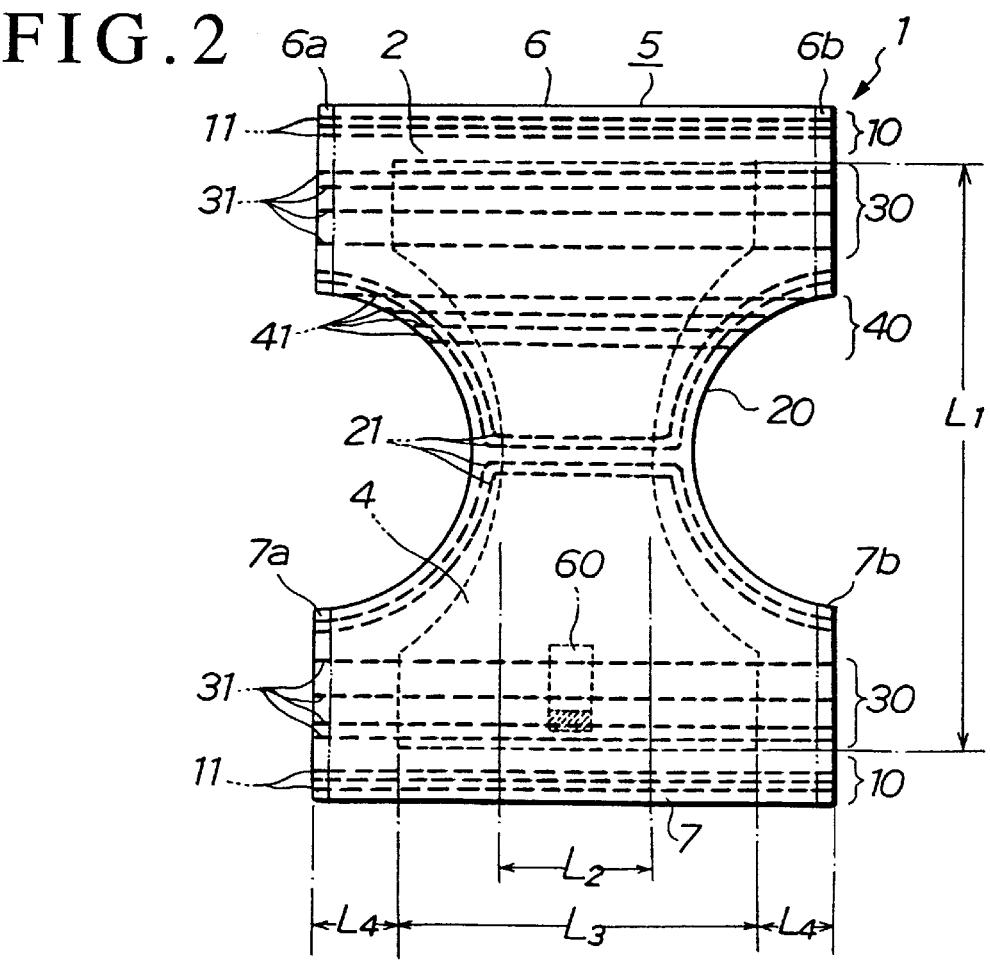
FIG. 2 is a plan view of the shorts type disposable diaper of FIG. 1 in an unfolded condition.
Figure 3:
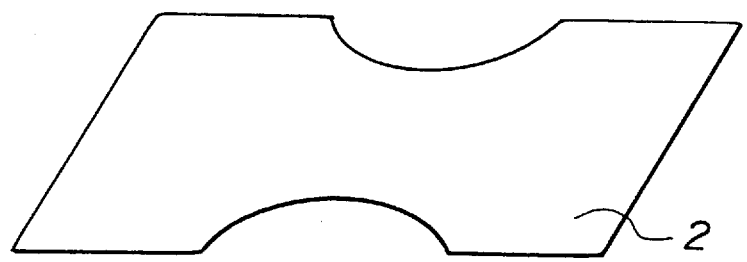
FIG. 3 is an exploded perspective view of the shorts type disposable diaper shown in FIG. 2 in an unfolded condition.
Figure 3:
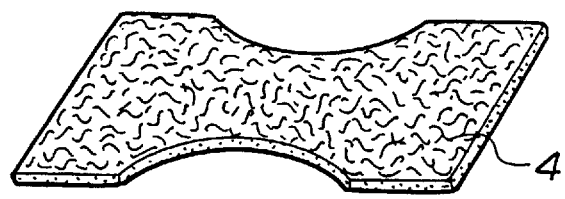
Figure 3:
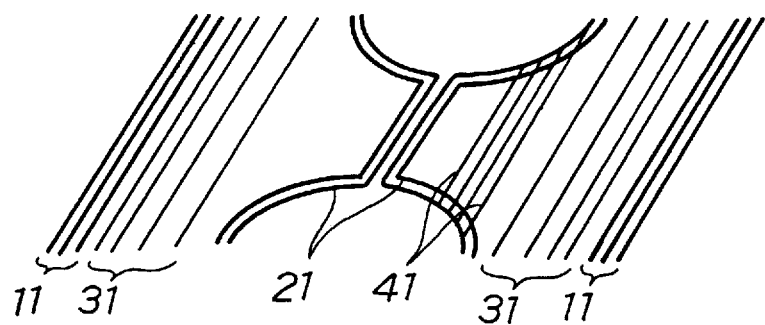
Figure 3:
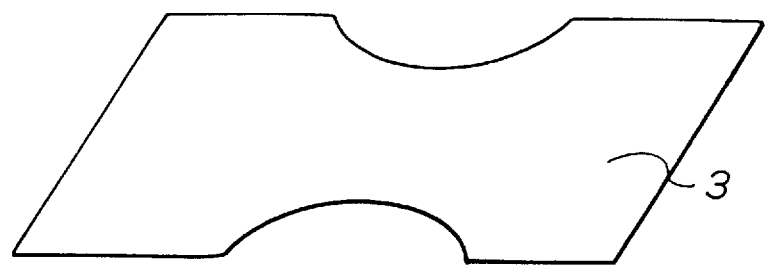
Figure 4:
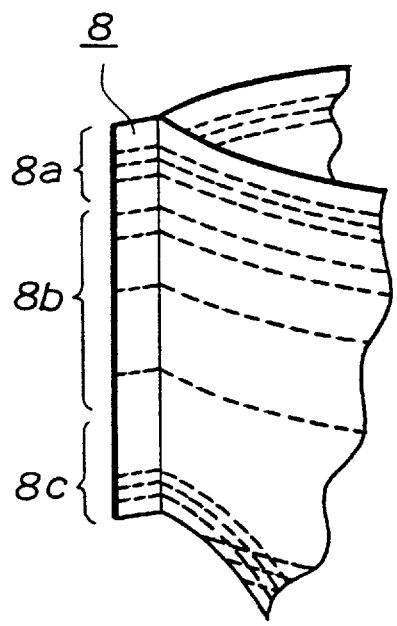
FIG. 4 is an enlarged perspective view of the joint portion 8 of the diaper shown in FIG. 1.
Figure 5:
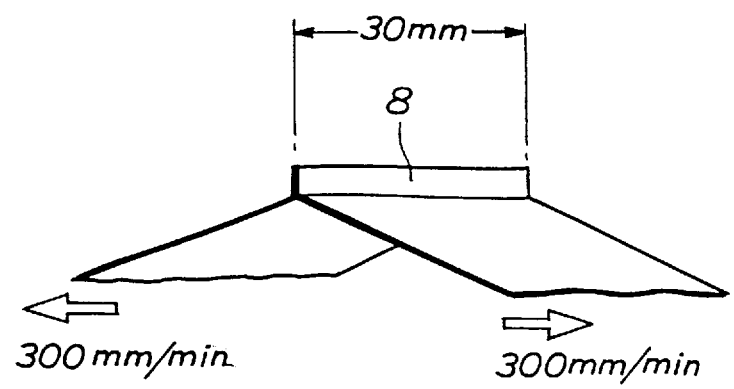
FIG. 5 is a schematic view illustrating the method of measuring the sealing strength of the joint portion 8.

FIG. 1 is a perspective view of an embodiment of a shorts type disposable diaper of the first invention. FIG. 2 is a plan view of the shorts type disposable diaper shown in FIG. 1 in its unfolded condition. FIG. 3 is an exploded perspective view of the shorts type disposable diaper shown in FIG. 2 in its unfolded condition. FIG. 4 is an enlarged perspective view showing a joint portion of the diaper shown in FIG. 1. FIG. 5 is a schematic view illustrating the method of measuring the sealing strength of the joint portion.

The shorts type disposable diaper 1 of the embodiment shown in FIGS. 1 to 3 comprises an absorbent body 5 which comprises a liquid permeable topsheet 2, a liquid impermeable backsheet 3, and an absorbent member 4 interposed between the topsheet 2 and the backsheet 3. Opposing lateral side edges of a front waist body portion 6 corresponding to the front waist side of a wearer and those of a rear waist body portion 7 corresponding to the rear waist side of a wearer are joined and sealed together thereby forming a waist opening portion 10 and a pair of leg opening portions 20.

Going into details, the lateral side edge 6a of the front waist body portion 6 and the lateral side edge 7a of the rear waist body portion 7 are joined and sealed together, and the lateral side edge 6b of the front waist body portion 6 and the lateral side edge 7b of the rear waist body portion 7 are joined and sealed together to form the joint portions 8 on each side.

The elastic members 11 and 21 are provided on the entire circumference of the waist opening portion 10 and the pair of leg opening portions 20, respectively, to form substantially continuous gathers. Further, a plurality of elastic members 31 are provided at a body-surrounding portion 30 which is located between the waist opening portion 10 and the pair of leg opening portions 20 and at which the absorbent member 4 is provided, to thereby form substantially continuous gathers along the entire circumference of the body-surrounding portion 30.

The opposing lateral side edges of the front and the rear waist body portions 6 and 7 are each provided on the topsheet 2, the backsheet 3,. and the elastic members 11, 21 and 31, and the corresponding side edges are joined and sealed together in such a manner that the corresponding side edges of the topsheet 2 are brought into contact with each other.

Three pieces of elastic members 11 are provided at the waist opening portion 10 of each of the front and rear waist body portions 6 and 7 at regular intervals. The elastic members 11 on the front waist body portion 6 and those on the rear waist body portion 7 are connected together by the above-mentioned joining and sealing to form substantially continuous gathers along the entire circumference of the waist opening portion 10.

Any of the elastic members conventionally employed in disposable diapers can be used as the elastic member 11 with no particular limitation. The elastic member 11 is a string or a band made of natural rubber, synthetic rubber, foamed polyurethane, etc. and is continuously joined to the topsheet 2 and the backsheet 3. In this embodiment, an elastic member of band form is used. The elongation of the elastic member preferably ranges from 80% to 140%. The term "elongation" as used herein has such a definition that when an elastic member having a length of e.g., 10 cm can be extended to 20 cm, that is, twice its own length, the elongation is 100%.

Two elastic members 21 are provided at the leg opening portions 20 of each of the front and rear waist body portions 6 and 7 at regular intervals. The elastic members 21 on the front waist body portion 6 and those on the rear waist body portion 7 each cross the absorbent member at the crotch portion of the diaper and are connected together by the above-mentioned joining and sealing to form substantially continuous gathers along the entire circumference of the leg opening portions 20.

Any of the elastic members conventionally employed in disposable diapers can be used as the elastic member 21 with no particular limitation. The elastic member 21 is a string or a band made of natural rubber, synthetic rubber, foamed polyurethane, etc. and is continuously joined to each of the topsheet 2 and the backsheet 3. In this embodiment, an elastic member of string form is used. The elongation of the elastic member 21 preferably ranges from 60% to 100%.

Four pieces of the elastic members 31 are provided at the body-surrounding portions 30 of each of the front and rear waist body portions 6 and 7 in such a manner that the interval of the elastic members becomes narrower towards the waist opening portion 10. The elastic members 31 on the front waist body portion 6 and those on the rear waist body portion 7 are connected by the aforesaid joining and sealing to form substantially continuous gathers along the entire circumference of the body-surrounding portion 30.

Any of the elastic members conventionally employed in disposable diapers can be used as the elastic member 31 with no particular limitation. The elastic member 31 preferably has a string form and an elongation of from 80% to 120%.

It is preferable that the elongation of elastic member 31 increases as it approaches the waist opening portion 10. The rate of increase in elongation is preferably about 40%.

As shown in FIGS. 1 and 2, the shorts type disposable diaper 1 according to this embodiment has four elastic members 41 arranged at regular intervals in the urination point 40 located below the body-surrounding portion 30 and in the vicinity of the urination portion of a wearer, to thereby form continuous gathers in the width direction of the diaper.

The term "in the vicinity of the urination portion" as referred to above means the portion corresponding to the urination portion of a wearer and the surrounding portions thereof. Specifically, it means the crotch portion of the front waist body portion 6 which is located between the pair of leg opening portions 20.

The topsheet 2, the backsheet 3, and the absorbent member 4 each has a sandglass shape with its central portion narrowed. These members can be fabricated of the following materials.

The topsheet 2 is made of a liquid permeable sheet which transmits excretions to the absorbent member 4 and preferably feels like underwear. Such a liquid permeable sheet preferably includes woven fabric, nonwoven fabric, and porous film. Leakage of urine, etc. due to oozing from the periphery of the topsheet 2 can be prevented by a water-repellent treatment comprising coating the peripheral portion of the topsheet 2 with a hydrophobic compound such as silicone oil and paraffin wax or once coating the entire surface of the topsheet 2 with a hydrophilic compound such as an alkyl phosphate and then washing the peripheral portion with warm water.

In this embodiment, nonwoven fabric having a mechanical strength of about 3500 gf/50 mm in the longitudinal direction of the diaper and of about 1500 gf/50 mm in the width direction of the diaper was used as the topsheet 2. That is, the longitudinal direction of continuous nonwoven web corresponds to the width direction of the diaper, and the width direction of the web to the longitudinal direction of the diaper.

A liquid impermeable and vapor permeable sheet obtained by stretching a filler-containing thermoplastic resin film is preferably used as the backsheet 3. Materials having a feeling close to underwear, such as a composite material composed of a film and nonwoven fabric or a composite material of a film and woven fabric, are used.

In this embodiment, a composite material composed of a film and nonwoven fabric and having a mechanical strength of about 3000 gf/50 mm in the longitudinal direction of the diaper and of about 600 gf/50 mm in the width direction of the diaper is used. That is, the longitudinal direction of continuous nonwoven web corresponds to the width direction of the diaper, and the width direction of the web to the longitudinal direction of the diaper.

The mechanical strength as referred to above is the maximum value as measured in accordance with JIS (Japanese Industrial Standard) L1096 6.12 at a distance of 150 mm between chucks.

A combination comprising comminuted pulp as a main component and an absorbent polymer is preferably used as a material of the absorbent member 4. Additionally, a heat-treated mixture of a thermoplastic resin, cellulose fiber and an absorbent polymer is also preferred. The absorbent polymer may be present in any of the upper, middle and lower layers of the absorbent member 4 and may be present as an admixture with pulp. The absorbent polymers preferably include those capable of absorbing and retaining 20 or more times its own weight of liquid and gelling on liquid absorption. Such absorbent polymers include a saponified starch-acrylic acid (or a salt thereof) graft copolymer, crosslinked sodium carboxymethyl cellulose, and an acrylic acid (or a salt thereof) polymer.

The absorbent member 4 preferably has the longitudinal length L1 of about 300 to about 600 mm (about 430 mm in this embodiment), the narrowest width L2 of about 80 to about 110 mm (about 100 mm in this embodiment), and the broadest width L3 of about 120 to about 350 mm (about 200 mm in this embodiment) in the opposing front and rear waist sides. The side flap of the diaper which extends from each side of the absorbent member 4 preferably has a width (L4) of about 10 to about 150 mm (about 90 mm in this embodiment).

As shown in FIG. 2, a fastening tape 60 for disposal is provided on the outer surface of the rear waist body portion 7. A used diaper can be disposed hygienically by means of the fastening tape 60.

The joint portion 8 is formed by a known sealing technique, such as ultrasonic sealing, heat sealing or radiofrequency sealing. In this embodiment, heat sealing is adopted.

Thus, the topsheet 2 and/or the backsheet 3 in shorts type disposable diaper 1 according to this embodiment have a mechanical strength of about 1500 gf/50 mm or more, preferably from about 2000 to 4500 gf/50 mm, in the longitudinal direction of the diaper. In this embodiment, the strength of the topsheet in the longitudinal direction is 3500 gf/50 mm, and that of the backsheet is 3000 gf/50 mm.

If the strength were less than 1500 gf/50 mm, when the joint portion 8 is torn apart in the longitudinal direction for disposal, a tear would initiate in the width direction of the diaper, making the manual tearing action difficult.

The mechanical strength as referred to above is the maximum value as measured in accordance with JIS (Japanese Industrial Standard) L1096 6.12 at a distance of 150 mm between chucks.

The joint portion 8 is roughly divided into three parts according to the gathers, i.e., a waist gathers part 8a, a body-surrounding part 8b, and a leg gathers part 8c as illustrated in FIG. 4. There is a possibility that these three parts are different in sealing strength, even sealed under the same conditions.

The parts 8a, 8b, and 8c each preferably have a sealing strength of not less than about 1000 gf/30 mm, still preferably from about 1000 to 3000 gf/30 mm, and particularly preferably from about 1500 to 2000 gf/30 mm, as measured as follows. The joint portion 8 is crosswise cut into 30 mm wide strips, and each strip is pulled in the directions indicated by arrows in FIG. 5, i.e., at a peel angle of 180°, at a pulling speed of 300 mm/min. The maximum force in the pulling is measured. In this embodiment, the above-mentioned three parts all have a sealing strength of about 1800 gf/30 mm in average.

That is, in the present invention, the sealing strength of opposing lateral side edge of the diaper forming the joint portion 8 is preferably about 1000 gf/30 mm or more.

If the sealing strength in each part exceeds 3000 gf/30 mm, it may be practically difficult to manually tear apart the joint portion 8. If it is less than 1000 gf/30 mm, the joint portion 8 may tend to be torn while the diaper is worn. Therefore, it is preferable that the sealing strength falls within the above-recited range.

Because of the above-mentioned structure, the shorts type disposable diaper of this embodiment does not suffer tearing at the joint portion 8 during use and is easy to manually tear apart at the joint portion 8 when it is to be removed from a wearer and disposed. When the joint portion 8 is torn apart, the material constituting the diaper does not undergo tearing in the width direction (at a right angle with the tearing direction).

While the embodiment of the first invention has been described with reference to a particular structure in which both the topsheet and the backsheet have a mechanical strength falling within the above-described specific range, any structure will do so long as either one of the topsheet and the backsheet satisfies the above requirement of mechanical strength.

Further, while the embodiment of the first invention has been described with reference to a particular structure in which each of the side edges is formed of two sheets, the topsheet and the backsheet, the side edges may be formed of either one of the topsheet and the backsheet and another compliant sheet. In other words, each of the side edges of the shorts type disposable diaper of the present invention may be formed of two sheets including at least the topsheet and/or the backsheet. At least one of the topsheet and the backsheet forming each side edge should satisfy the aforesaid strength requirement in the longitudinal direction of the diaper. It is preferable that the joint portion 8 at which the two sheets are joined and sealed has a sealing strength of about 1000 gf/30 mm or more.

A preferred embodiment of the second invention will be illustrated with reference to FIG. 6.

Figure 6:
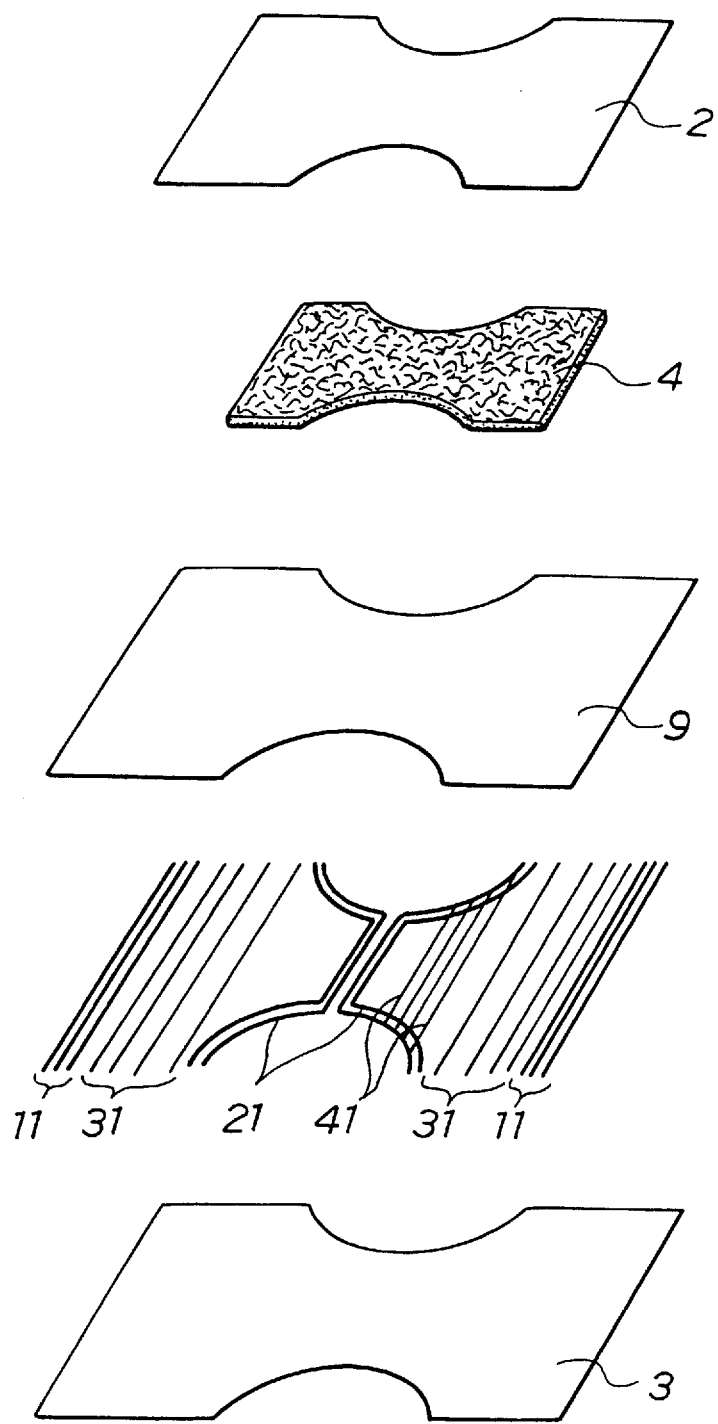
FIG. 6 is an exploded perspective view (corresponding to FIG. 3) of a shorts type disposable diaper according to the second invention in an unfolded condition.

FIG. 6 is an exploded perspective view of a shorts type disposable diaper according to the second invention in an unfolded condition (corresponding to FIG. 3). Unless particularly described in detail, the explanation given to the embodiment of the first invention applies to the following embodiment appropriately.

Similarly to the embodiment of the first invention shown in FIGS. 1 and 2, a shorts type disposable diaper 1 of this embodiment comprises an absorbent body 5 which comprises a liquid permeable topsheet 2, a liquid impermeable backsheet 3, and an absorbent member 4 interposed therebetween. Opposing lateral side edges of a front waist body portion 6 corresponding to the front waist side of a wearer and those of a rear waist body portion 7 corresponding to the rear waist side of a wearer are joined and sealed together thereby forming a waist opening portion 10 and a pair of leg opening portions 20.

The side edges 6a and 6b are joined and sealed with the side edge 7a and 7b, respectively, to form joint portions 8 on each side of the diaper. The elastic members 11 and 21 are provided on the entire circumference of the waist opening portion 10 and the pair of leg opening portions 20, respectively, to form substantially continuous gathers. Further, a plurality of elastic members 31 are provided at a body-surrounding portion 30 which is located between the waist opening portion 10 and the pair of leg opening portions 20 and at which the absorbent member 4 is located, to thereby form substantially continuous gathers along the entire circumference of the body-surrounding portion 30.

The above-mentioned structure is the same as in the embodiment of the first invention.

In the embodiment of the second invention shown in FIG. 6, the topsheet 2 is made smaller than the backsheet 3 and the covering sheet 9 covering the elastic members, being sized just enough to cover the absorbent member 4. Similarly to the embodiment of the first invention, a fastening tape 60 which may be used at the time of disposal is provided on the outer surface of the backsheet 3 of the rear waist body portion 7. When a used diaper, particularly after the solid waste materials are discharged, is disposed, the diaper can be folded or rolled up and fastened with the fastening tape 60.

In the shorts type disposable diaper 1 of the second invention shown in FIG. 6, the absorbent body 5 has a covering sheet 9 for the elastic members which is disposed between the absorbent member 4 and the backsheet 3, and the opposing lateral side edges of the front and rear waist body portions 6 and 7 comprise the covering sheet 9 for the elastic members, a backsheet 3, and elastic members 11, 21, and 31. The lateral side edges are joined and sealed together in such a manner that the lateral side edges of the covering sheet of the front waist body portion 6 and the corresponding lateral side edges of the covering sheet of the rear waist body portion 7 are brought into contact with each other.

The elastic members 11, 21, 31, and 41 are each sandwiched and fixed between the covering sheet 9 and the backsheet 3.

In the shorts type disposable diaper according to the present invention, at least one of the covering sheet 9 and the backsheet 3 has a mechanical strength of about 1,500 gf/50 mm or more, preferably from about 2000 to 5000 gf/50 mm, in the longitudinal direction of the diaper.

If the strength were less than 1500 gf/50 mm, when the joint portion 8 is torn apart in the longitudinal direction for disposal, a tear would initiate in the width direction of the diaper, making the manual tearing action difficult.

The covering sheet 9 for the elastic members preferably comprises nonwoven fabric, etc. which has water repellency and air permeability and feels like underwear. The covering sheet 9 for the elastic members preferably has a mechanical strength of about 4000 gf/50 mm or more, still preferably from about 4500 to 8500 gf/50 mm, in the width direction of the diaper (in the machine direction of the nonwoven fabric web forming the covering sheet) and of from about 2000 to 5000 gf/50 mm in the longitudinal direction of the diaper (in the width direction of the nonwoven fabric web forming the covering sheet).

In this embodiment, nonwoven fabric which has not been rendered hydrophobic is used as the covering sheet. The strength of the nonwoven fabric is about 3000 gf/50 mm in the longitudinal direction of the diaper (in the width direction of the nonwoven fabric web) and is about 5000 gf/50 mm in the width direction of the diaper (in the machine direction of the nonwoven fabric web). That is, continuous nonwoven web is used as the covering sheet 9 with its longitudinal direction as a width direction of the diaper and its width direction as a longitudinal direction of the diaper.

In this embodiment, nonwoven fabric is used as the topsheet 2. The nonwoven fabric has a mechanical strength of about 600 gf/50 mm in the longitudinal direction and of about 2500 gf/50 mm in the width direction. A composite material composed of a film and nonwoven fabric is used as the backsheet 3. The nonwoven fabric of the composite material has a mechanical strength of about 600 gf/50 mm in the longitudinal direction and about 2500 gf/50 mm in the width direction, and the composite material has a mechanical strength of about 600 gf/50 mm in the longitudinal direction and about 3000 gf/50 mm in the width direction.

In this embodiment, the opposing lateral side edges of the diaper forming the joint portion 8 has a sealing strength of about 1000 gf/30 mm in average in each of the above-mentioned three parts.

Also in the shorts type disposable diaper of this embodiment, the similar advantageous effects to those obtained in the embodiment of the first invention can be produced. In addition, since the topsheet 2 and the covering sheet 9 for the elastic members are separately provided, it is feasible to provide a product having an excellent feeling when worn by fabricating the topsheet 2 of sheeting with good texture and fabricating, for example, the covering sheet 9 of sheeting having the above-described mechanical strength.

While the embodiment of the second invention has been described with reference to a particular structure in which only the covering sheet 9 for the elastic members has such a strength as falls within the above-described specific range, the present invention is not limited thereto. That is, the backsheet 3 may also be fabricated of a material having such a strength as falls within that range. Further, while the embodiment of the second invention has been described with a particular structure in which the joint portion 8 is composed of the covering sheet 9 and the backsheet 3, it may be composed of covering the sheet 9, the topsheet 2, and the backsheet 3. In this case, the topsheet 2 may also be fabricated of a material having such a strength as falls within the above-mentioned specific range. Other modifications can be made in the present invention without departing from the spirit and scope of the present invention.

Industrial Applicability

The shorts type disposable diaper according to the present invention can easily be torn apart at the joint portion thereof and is therefore convenient for use.

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

We claim:

1. A shorts type disposable diaper comprising an absorbent body which comprises a liquid permeable topsheet, a liquid impermeable backsheet, an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, the topsheet and/or the backsheet have a mechanical strength of about 1,500 gf/50 mm or more in the longitudinal direction of the diaper, the opposing lateral side edges of the front and rear waist body portions to be sealed together are provided on at least two sheets including the topsheet and/or the back-sheet to form a joint portion, a maximum force is measured in such a manner that the joint portion is crosswise cut into 30 mm wide strips, and each strip is pulled at a peel angle of 180° at a pulling speed of 300 mm/min, wherein the sealing strength at the opposing lateral side edges of the joint portion is about 1,000 gf/30 mm or more, said joint portion being able to be torn in the longitudinal direction between said waist opening portion and said leg opening portion without tearing occurring in the width direction of the diaper.

2. The shorts type disposable diaper according to claim 1, wherein each of the waist opening portion and the pair of leg opening portions is provided with an elastic member which forms substantially continuous gathers along the entire circumference of the waist opening portion and the leg opening portions.

3. The shorts type disposable diaper according to claim 1, wherein a plurality of elastic members are provided at a body-surrounding portion which is located between the waist opening portion and the pair of leg opening portions and at which the absorbent member is provided, forming substantially continuous gathers along the entire circumference of the body-surrounding portion.

4. A shorts type disposable diaper comprising an absorbent body which comprises a liquid permeable topsheet, a liquid impermeable backsheet, and an absorbent member interposed between the topsheet and the backsheet, the absorbent body having a front waist body portion located on the stomach side of a diaper wearer when the diaper is worn and a rear waist body portion located on the back side of the wearer, the front and rear waist body portions being joined and sealed together at opposing lateral side edges thereof to form a waist opening portion and a pair of leg opening portions, the absorbent body has a covering sheet for covering elastic members, the covering sheet being disposed between said absorbent member and said backsheet, the opposing lateral side edges of the front and rear waist body portions are provided on said covering sheet and said backsheet, the opposing lateral side edges of the front and rear waist body portions are sealed together in such a manner that the covering sheet at the opposing lateral side edges is brought into contact with each other to form a joint portion, at least one of said covering sheet and said backsheet has a mechanical strength of about 1,500 gf/50 mm or more in the longitudinal direction of the diaper, a maximum force is measured in such a manner that the joint portion is crosswise cut into 30 mm wide strips, and each strip is pulled at a peel angle of 180° at a pulling speed of 300 mm/min, wherein the sealing strength at the opposing lateral side edges of the joint portion is about 1,000 gf/30 mm or more, said joint portion being able to be torn in the longitudinal direction between said waist opening portion and said leg opening portion without tearing occurring in the width direction of the diaper.

5. The shorts type disposable diaper according to claim 4, wherein each of the waist opening portion and the pair of leg opening portions is provided with an elastic member which forms substantially continuous gathers along the entire circumference of the waist opening portion and the leg opening portions.

6. The shorts type disposable diaper according to claim 4, wherein a plurality of elastic members are provided at a body-surrounding portion which is located between the waist opening portion and the pair of leg opening portions and at which the absorbent member is provided, forming substantially continuous gathers along the entire circumference of the body-surrounding portion.

* * * * *